United States Patent [19]

Richter et al.

[11] 3,959,478

[45] May 25, 1976

[54] INSECTICIDAL 2-PHENYL-4-BENZOYL-1,2,4-OXADIAZOLIDINE-3,5-DIONES

[75] Inventors: Sidney B. Richter, Chicago; Leonard J. Stach, Riverside; Robert N. Wilke, Chicago, all of Ill.

[73] Assignee: Velsicol Chemical Corporation, Chicago, Ill.

[22] Filed: Mar. 17, 1975

[21] Appl. No.: 558,577

[52] U.S. Cl. ............................. 424/272; 260/307 B
[51] Int. Cl.² ....................................... C07D 271/06
[58] Field of Search ............... 260/307 B; 424/272, 424/74 H

[56] References Cited
OTHER PUBLICATIONS
Zinner et al. – C. A. 64, 11201g (1966).

*Primary Examiner*—Raymond V. Rush
*Attorney, Agent, or Firm*—Robert J. Schwarz; Dietmar H. Olesch

[57] ABSTRACT

This invention discloses chemical compounds having the following structural formula

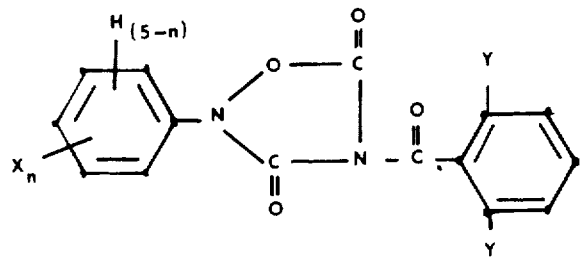

wherein X is chlorine or fluorine; n is an integer from 1 to 3; and Y is chlorine, bromine or fluorine. The compounds of the above description are useful as insecticides.

9 Claims, No Drawings

INSECTICIDAL 2-PHENYL-4-BENZOYL-1,2,4-OXADIAZOLIDINE-3,5-DIONES

This invention relates to new compositions of matter and more specifically relates to new chemical compounds of the formula

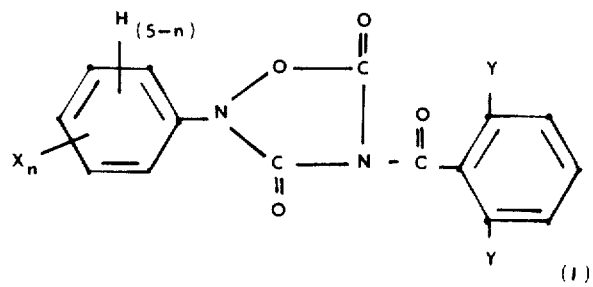

(I)

wherein X is chlorine or fluorine; n is an integer from 1 to 3; and Y is chlorine, bromine or fluorine.

The compounds of the present invention are unexpectedly useful as insecticides.

The compounds of the present invention can be conveniently prepared by reacting an oxadiazolidine of the formula

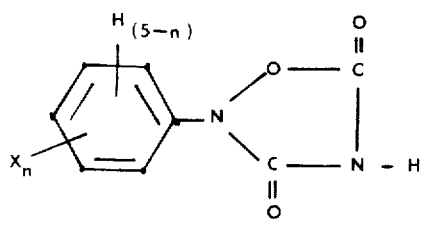

(II)

wherein X and n are as heretofore described, with a benzoyl chloride of the formula

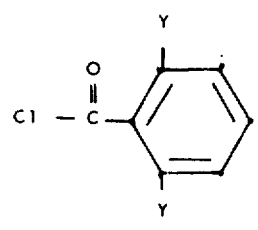

(III)

wherein Y is as heretofore described. This reaction can be effected by combining about equimolar amounts of the oxadiazolidine and benzoyl chloride in an inert organic reaction medium, such as toluene, in the presence of an acid acceptor such as a tertiary amine or alkali metal carbonate or bicarbonate. The reaction mixture can then be heated at the reflux temperature of the mixture for a period of from 4 to 48 or more hours. After this time the reaction mixture can be filtered to remove acid acceptor halide and can be washed with water and dilute inorganic acid. The washed solution can then be dried and stripped of solvent to yield the desired product as the residue. This product can be used as such or can be further purified by conventional means such as recrystallization and the like.

The compounds of formula II can be prepared by reacting a hydroxyurea of the formula

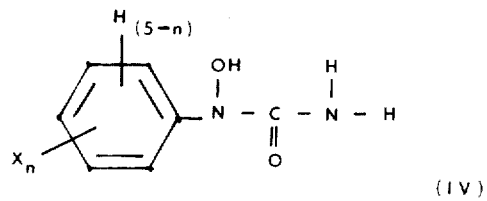

(IV)

wherein X and n are as heretofore described, with an alkyl chloroformate such as ethyl chloroformate. This reaction can be conveniently carried out in aqueous base such as aqueous sodium hydroxide solution by adding the alkyl chloroformate to an about equimolar amount of the hydroxyurea at lower temperatures such as at 5°–20°C. The addition is preferably performed with stirring and the stirring continued after the the addition. The desired compound can then be recovered and purified by conventional techniques such as filtration, decantation, extraction, washing, drying, recrystallizing and the like.

The hydroxyureas of formula IV when not readily available can be conveniently prepared from the corresponding arylhydroxylamine by reaction with potassium cyanate.

Exemplary ureas of formula IV are 1-(4-chlorophenyl)-1-hydroxyurea, 1-(4-fluorophenyl)-1-hydroxyurea, 1-(3,4-dichlorophenyl)-1-hydroxyurea, 1-(3,4,5-trichlorophenyl)-1-hydroxyurea, 1-(3,4-difluorophenyl)-1-hydroxyurea, 1-(3-chlorophenyl)-1-hydroxyurea, 1-(2,4,6-trichlorophenyl)-1-hydroxyurea and the like.

Exemplary benzoyl chlorides of formula III useful in preparing the compounds of this invention are 2,6-dichlorobenzoyl chloride, 2,6-dibromobenzoyl chloride and 2,6-difluorobenzoyl chloride.

The manner in which the compounds of the present invention can be prepared is more specifically illustrated in the following examples.

EXAMPLE 1

Preparation of 2-(3,4-Dichlorophenyl)-1,2,4-oxadiazolidin-3,5-dione 1-(3,4-Dichlorophenyl)-1-hydroxyurea (6.0 grams) dissolved in aqueous sodium hydroxide (13 ml; 2.0 M) is charged into a glass reaction vessel equipped with a mechanical stirrer and thermometer. The reaction mixture is cooled to a temperature of 10° to 15°C and ethyl chloroformate (2.5 ml) is slowly added with stirring resulting in the formation of a white precipitate. After the addition is completed stirring is continued for a period of about ½ hour. After this time the reaction mixture is poured into a water-ice mixture and is treated with 6 N hydrochloric acid until the mixture is acidic. The solid product is then recovered by filtration and is dissolved in methylene chloride. The resulting solution is dried over anhydrous magnesium sulfate and is stripped of solvent. The remaining solid residue is then recrystallized from toluene to yield the desired product 2-(3,4-dichlorophenyl)-1,2,4-oxadiazolidin-3,5-dione having a melting point of 126° to 127.5°C.

EXAMPLE 2

Preparation of
2-(3,4-Dichlorophenyl)-4-(2,6-dichlorobenzoyl)-1,2,4-oxadiazolidin-3,5-dione 2-(3,4-Dichlorophenyl)-1,2,4-oxadiazolidin-3,5-dione (4.0 grams) and aqueous sodium hydroxide (20 ml; 2 M) are charged into a glass reaction flask at 0°C and stirred for a period of about 1 hour. Water is then added until all the solid is dissolved. The reaction mixture is then treated with 6 N hydrochloric acid to precipitate a tan solid. This solid is dissolved in ether and the ether solution is dried over anhydrous magnesium sulfate. The dried solution is then stripped of solvent to yield purified 2-(3,4-dichlorophenyl)-1,2,4-oxadiazolidin-3,5-dione. This purified product (2.8 grams), methylene chloride (10 ml) and triethylamine (1.3 grams) are charged into a glass reaction vessel equipped with a mechanical stirrer and thermometer. 2,6-Dichlorobenzoyl chloride (2.3 grams) dissolved in ethylene chloride (5 ml) is then added to the reaction flask with stirring at a temperature of 20° to 30°C. The reaction mixture is then stirred for a period of one hour and is stripped of solvent in a rotary evaporator to yield a residue. The residue is then dissolved in a benzene-hexane mixture and is heated at reflux for a period of about 3 hours. The reaction mixture is then allowed to cool to room temperature and is allowed to stand for several days. After this time the reaction mixture is filtered and the filtrate is washed with dilute hydrochloric acid, water and with dilute sodium carbonate. The washed solution is then filtered and the filtrate is again washed with water, is dried and is stripped of solvent to yield a residue. This residue was recrystallized from ethanol to yield the desired product 2-(3,4-dichlorophenyl)-4-(2,6-dichlorobenzoyl)-1,2,4-oxadiazolidin-3,5-dione as a light yellow solid having a melting point of 122° to 124°C.

EXAMPLE 3

Preparation of
2-(4-Chlorophenyl)-1,2,4-oxadiazolidin-3,5-dione 1-(4-Chlorophenyl)-1-hydroxyurea (34 grams; 0.18 mole) dissolved in aqueous sodium hydroxide (200 ml; 2 N) are charged into a glass reaction vessel equipped with a mechanical stirrer and thermometer. The solution is cooled to a temperature of 10° to 15°C and ethyl chloroformate (17 ml) is slowly added with stirring. After the addition is completed stirring is continued for a period of about ½ hour. Water (200 ml) is then added to the reaction mixture with stirring and the resulting mixture is poured into 3 liters of water. The resulting aqueous solution is then filtered and the filtrate is cooled and acidified with concentrated hydrochloric acid to form a precipitate. The precipitate is recovered by filtration and is dried. The resulting product is then dissolved in a 100:5 mixture of methylene chloride and tetrahydrofuran and the solution is dried over anhydrous magnesium sulfate. The dried solution is then stripped of solvent under reduced pressure to yield the desired product 2-(4-chlorophenyl)-1,2,4-oxadiazolidin-3,5-dione.

EXAMPLE 4

Preparation of
2-(4-Chlorophenyl)-4-(2,6-dichlorobenzoyl)-1,2,4-oxadiazolidin-3,5-dione 2-(4-Chlorophenyl)-1,2,4-oxadiazolidin-3,5-dione (3.8 grams; 0.018 mole), toluene (50 ml) and triethylamine (2.8 ml) are charged into a glass reaction vessel equipped with a mechanical stirrer, thermometer and reflux condenser. 2,6-Dichlorobenzoyl chloride (4.19 grams) dissolved in toluene (10 ml) is then added to the reaction flask and the resulting mixture is heated at reflux with stirring for a period of about 3 days. After this time the reaction mixture is filtered and the filtrate is washed with water, dilute hydrochloric acid and with aqueous sodium bicarbonate. The washed solution is then dried over anhydrous magnesium sulfate, is filtered and is stripped of solvent under reduced pressure. The residue is washed with a hexane-ether mixture to yield a brown solid. This solid is recrystallized from a benzene-hexane mixture to yield the desired product 2-(4-chlorophenyl)-4-(2,6-dichlorobenzoyl)-1,2,4-oxadiazolidin-3,5-dione having a melting point of 112° to 116°C.

EXAMPLE 5

Preparation of
2-(3,4-Difluorophenyl)-1,2,4-oxadiazolidin-3,5-dione 1-(3,4-Difluorophenyl)-1-hydroxyurea (0.2 mole) dissolved in aqueous sodium hydroxide (200 ml; 2N) is charged into a glass reaction vessel equipped with a mechanical stirrer and thermometer. The solution is cooled to a temperature of about 10°C and ethyl chloroformate (0.21 mole) is slowly added with stirring. After the addition is completed stirring is continued for a period of about one hour. The reaction mixture is then poured into 2 liters of water. The resulting aqueous solution is then filtered and the filtrate is cooled and acidified with concentrated hydrochloric acid to form a precipitate. The precipitate is recovered by filtration and is dried. The dried product is then dissolved in a methylene chloride-tetrahydrofuran mixture and the resulting solution is dried over anhydrous magnesium sulfate, filtered and stripped of solvent to yield the desired product 2-(3,4-difluorophenyl)-1,2,4-oxadiazolidin-3,5-dione as the residue.

EXAMPLE 6

Preparation of
2-(3,4-Difluorophenyl)-4-(2,6-dichlorobenzoyl)-1,2,4-oxadiazolidin-3,5-dione 2-(3,4-Difluorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Dichlorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(3,4-difluorophenyl)-4-(2,6-dichlorobenzoyl)-1,2,4-oxadiazolidin-3,5-dione.

EXAMPLE 7

Preparation of
2-(3-Chlorophenyl)-1,2,4-oxadiazolidin-3,5-dione 1-(3-Chlorophenyl)-1-hydroxyurea (0.2 mole) dissolved in aqueous sodium hydroxide (200 ml; 2 N) is charged into a glass reaction vessel equipped with a mechanical stirrer and thermometer. The solution is cooled to a temperature of about 10°C and ethyl chloroformate (0.21 mole) is slowly added with stirring. After the addition is completed stirring is continued for a period of about one hour. The reaction mixture is then poured into 2 liters of water. The resulting aqueous solution is then filtered and the filtrate is cooled and acidified with concentrated hydrochloric acid to form a precipitate. The precipitate is recovered by filtration and is dried. The dried product is then dissolved in a methylene chloride-tetrahydrofuran mixture and the resulting solution is dried over anhydrous magnesium sulfate, filtered and stripped of solvent to yield the desired product 2-(3-chlorophenyl)-1,2,4-oxadiazolidin-3,5-dione as the residue.

EXAMPLE 8

Preparation of
2-(3-Chlorophenyl)-4-(2,6-dichlorobenzoyl)-1,2,4-oxadiazolidin-3,5-dione 2-(3-Chlorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Dichlorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(3-chlorophenyl)-4-(2,6-dichlorobenzoyl)-1,2,4-oxadiazolidin-3,5-dione.

EXAMPLE 9

Preparation of
2-(4-Chlorophenyl)-4-(2,6-difluorobenzoyl)-1,2,4-oxadiazolidin-3,5-dione 2-(4-Chlorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Difluorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(4-chlorophenyl)-4-(2,6-difluorobenzoyl)-1,2,4-oxadiazolidin-3,5-dione.

EXAMPLE 10

Preparation of
2-(3,4-Dichlorophenyl)-4-(2,6-difluorobenzoyl)-1,2,4-oxadiazolidin-3,5-dione 2-(3,4-Dichlorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Difluorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(3,4-dichlorophenyl)-4-(2,6-difluorobenzoyl)-1,2,4-oxadiazolidin-3,5-dione.

EXAMPLE 11

Preparation of
2-(3,4,5-Trichlorophenyl)-1,2,4-oxadiazolidin-3,5-dione 1-(3,4,5-Trichlorophenyl)-1-hydroxyurea (0.2 mole) dissolved in aqueous sodium hydroxide (200 ml; 2 N) is charged into a glass reaction vessel equipped with a mechanical stirrer and thermometer. The solution is cooled to a temperature of about 10°C and ethyl chloroformate (0.21 mole) is slowly added with stirring. After the addition is completed stirring is continued for a period of about one hour. The reaction mixture is then poured into 2 liters of water. The resulting aqueous solution is then filtered and the filtrate is cooled and acidified with concentrated hydrochloric acid to form a precipitate. The precipitate is recovered by filtration and is dried. The dried product is then dissolved in a methylene chloride-tetrahydrofuran mixture and the resulting solution is dried over anhydrous magnesium sulfate, filtered and stripped of solvent to yield the desired product 2-(3,4,5-trichlorophenyl)-1,2,4-oxadiazolidin-3,5-dione.

EXAMPLE 12

Preparation of
2-(3,4,5-Trichlorophenyl)-4-(2,6-dibromobenzoyl)-1,2,4-oxadiazolidin-3,5-dione 2-(3,4,5-Trichlorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Dibromobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(3,4,5-trichlorophenyl)-4-(2,6-dibromobenzoyl)-1,2,4-oxadiazolidin-3,5-dione.

EXAMPLE 13

Preparation of 2-(4-Fluorophenyl)-1,2,4-oxadiazolidin-3,5-dione 1-(4-Fluorophenyl)-1-hydroxyurea (0.2 mole) dissolved in aqueous sodium hydroxide (200 ml; 2 N) is charged into a glass reaction vessel equipped with a mechanical stirrer and thermometer. The solution is cooled to a temperature of about 10°C and ethyl chloroformate (0.21 mole) is slowly added with stirring. After the addition is completed stirring is continued for a period of about one hour. The reaction mixture is then poured into 2 liters of water. The resulting aqueous solution is then filtered and the filtrate is cooled and acidified with concentrated hydrochloric acid to form a precipitate. The precipitate is recovered by filtration and is dried. The dried product is then dissolved in a methylene chloridetetrahydrofuran mixture and the resulting solution is dried over anhydrous magnesium sulfate, filtered and stripped of solvent to yield the desired product 2-(4-fluorophenyl)-1,2,4-oxadiazolidin-3,5-dione as the residue.

EXAMPLE 14

Preparation of 2-(4-Fluorophenyl)-4-(2,6-difluorobenzoyl)-1,2,4-oxadiazolidin-3,5-dione 2-(4-Fluorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Difluorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(4-fluorophenyl)-4-(2,6-difluorobenzoyl)-1,2,4-oxadiazolidin-3,5-dione.

EXAMPLE 15

Preparation of 2-(3-Chlorophenyl)-4-(2,6-difluorobenzoyl)-1,2,4-oxadiazolidin-3,5-dione 2-(3-Chlorophenyl)-1,2,4-oxadiazolidin-3,5-dione (0.03 mole), toluene (100 ml) and triethylamine (5 ml) are charged into a glass reaction vessel equipped with a mechanical stirrer, thermometer and reflux condenser. 2,6-Difluorobenzoyl chloride (0.03 mole) dissolved in toluene (20 ml) is then added to the reaction flask and the resulting mixture is heated at reflux with stirring for a period of about 24 hours. After this time the reaction mixture is filtered and the filtrate is washed with water, dilute hydrochloric acid and with aqueous sodium bicarbonate. The washed solution is then dried over anhydrous magnesium sulfate. The dried solution is stripped of solvent under reduced pressure leaving a solid residue. The residue is recrystallized to yield the desired product 2-(3-chlorophenyl)-4-(2,6-difluorobenzoyl)-1,2,4-oxadiazolidin-3,5-dione.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wet-table powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in the quantities are in parts by weight.

EXAMPLE 16

Preparation of a Dust

| | |
|---|---|
| Product of Example 2 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, [bis(2-thiocyanoethyl)ether], isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants, can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the bottom boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of this invention was demonstrated by carrying out the following test procedures. The results of each of these procedures are set forth in Table I.

SOUTHERN ARMYWORM--STOMACH POISON

Foliar portions of potted Dwarf Horticultural bean plants in first true leaf growth stage are dipped in agitated test solution containing the compounds of this invention, allowed to air dry and removed to holding racks provided with a subterranean water source. Three test plants are used for each test unit. Five third-instar larvae of Southern Armyworm are caged on treated plants for 72 hours. After this time observations are made for insect mortality.

MOSQUITO

Aliquots of 100 ml of tap water containing various concentrations of test compound were each supplied with 20 1-day-old Yellow Fever Mosquito larvae (*aedes aegypti* L.). The larvae were maintained at 25°C and were fed with malt yeast powder. After 13 days, when the pupae of untreated insects had hatched, the mortality percentages were calculated in comparison with the untreated controls.

TABLE I

|  | Rate ppm | % Mortality Product of Example 2 | Product of Example 4 |
|---|---|---|---|
| Southern Armyworm | 100 | 100 | 90 |
|  | 30 | 100 | 83 |

TABLE I-continued

|  | Rate ppm | % Mortality Product of Example 2 | Product of Example 4 |
|---|---|---|---|
| Mosquito | 10 | 93 | 67 |
|  | 3 | 17 | 3 |
|  | 1.00 | 100 | 93 |
|  | 0.30 | 100 | 67 |
|  | 0.10 | 100 | 47 |
|  | 0.03 | 38 | 0 |

We claim:
1. A compound of the formula

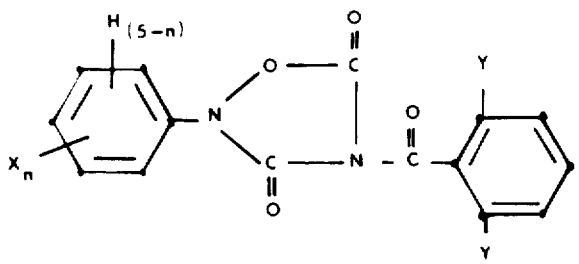

wherein X is chlorine or fluorine; n is an integer from 1 to 3; and Y is chlorine, bromine or fluorine.

2. The compound of claim 1, 2-(3,4-dichlorophenyl)-4-(2,6-dichlorobenzoyl)-1,2,4-oxadiazolidin-3,5-dione.

3. The compound of claim 1, 2-(4-chlorophenyl)-4-(2,6-dichlorobenzoyl)-1,2,4-oxadiazolidin-3,5-dione.

4. The compound of claim 1, 2-(3,4-difluorophenyl)-4-(2,6-dichlorobenzoyl)-1,2,4-oxadiazolidin-3,5-dione.

5. The compound of claim 1, 2-(3-chlorophenyl)-4-(2,6-dichlorobenzoyl)-1,2,4-oxadiazolidin-3,5-dione.

6. The compound of claim 1, 2-(4-chlorophenyl)-4-(2,6-difluorobenzoyl)-1,2,4-oxadiazolidin-3,5-dione.

7. The compound of claim 1, 2-(3,4-dichlorophenyl)-4-(2,6-difluorobenzoyl)-1,2,4-oxadiazolidin-3,5-dione.

8. A method of controlling insects which comprises contacting said insects with an insecticidal composition comprising an inert carrier and an insecticidally effective amount of a compound of claim 1.

9. An insecticidal composition comprising an inert carrier and an insecticidally effective amount of a compound of claim 1.

* * * * *